United States Patent
Thomas

(10) Patent No.: US 9,913,765 B2
(45) Date of Patent: Mar. 13, 2018

(54) DIAPER CHANGING ASSEMBLY

(71) Applicant: Bertha Thomas, Palmyra, VA (US)

(72) Inventor: Bertha Thomas, Palmyra, VA (US)

( * ) Notice: Subject to any disclaimer, the term of this patent is extended or adjusted under 35 U.S.C. 154(b) by 670 days.

(21) Appl. No.: 14/509,794

(22) Filed: Oct. 8, 2014

(65) Prior Publication Data

US 2016/0101002 A1    Apr. 14, 2016

(51) Int. Cl.
*A61F 13/15*    (2006.01)
*A61F 13/551*    (2006.01)
*A61F 13/84*    (2006.01)

(52) U.S. Cl.
CPC .... *A61F 13/55105* (2013.01); *A61F 13/5512* (2013.01); *A61F 2013/55125* (2013.01); *A61F 2013/8402* (2013.01); *B65D 2313/08* (2013.01)

(58) Field of Classification Search
CPC .................. A61F 13/84; A61F 13/8402; A61F 2013/8402; A61F 13/5512; B65D 2313/08
USPC ........................... 604/385.06, 385.02, 385.13
See application file for complete search history.

(56) References Cited

U.S. PATENT DOCUMENTS

| | | |
|---|---|---|
| 4,221,221 A | 9/1980 | Ehrlich |
| 4,743,240 A * | 5/1988 | Powell .................. A61F 13/551 604/385.13 |
| 4,808,175 A | 2/1989 | Hansen |
| 4,931,052 A | 6/1990 | Feldman |
| 5,582,605 A | 12/1996 | Lepie |
| D380,829 S | 7/1997 | Breault |
| 6,475,204 B1 | 11/2002 | Walker |
| 8,292,863 B2 | 10/2012 | Donoho |
| 2005/0203476 A1 | 9/2005 | Stegall |
| 2006/0217675 A1 | 9/2006 | Coelho |

* cited by examiner

*Primary Examiner* — Jacqueline Stephens

(57) ABSTRACT

A diaper changing assembly includes a bag removably coupled to a diaper. The bag is available when the diaper is changed. A first packet is positioned within the bag. The first packet contains a salve. The salve may be applied to a user when the diaper is changed. A second packet is positioned within the bag. The second packet contains a powder. The powder may be applied to the user when the diaper is changed. A plurality of wipes is positioned within the bag. The wipes may be used to clean the user when the diaper is changed.

8 Claims, 5 Drawing Sheets

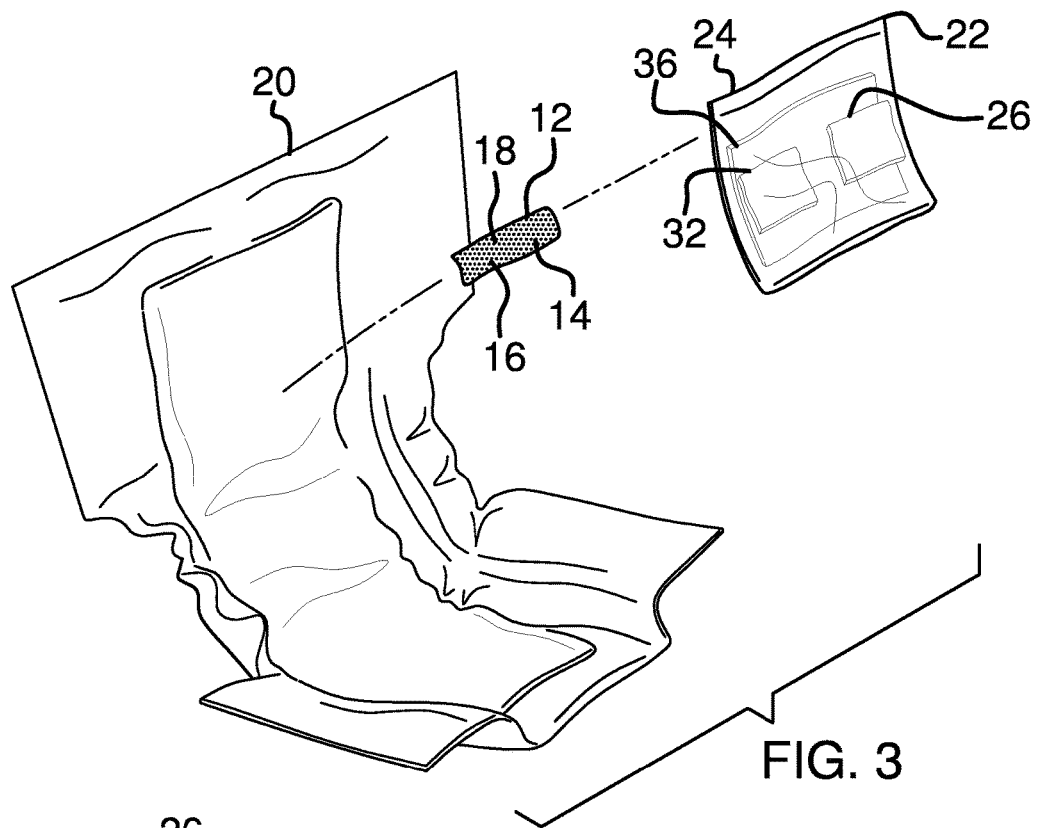
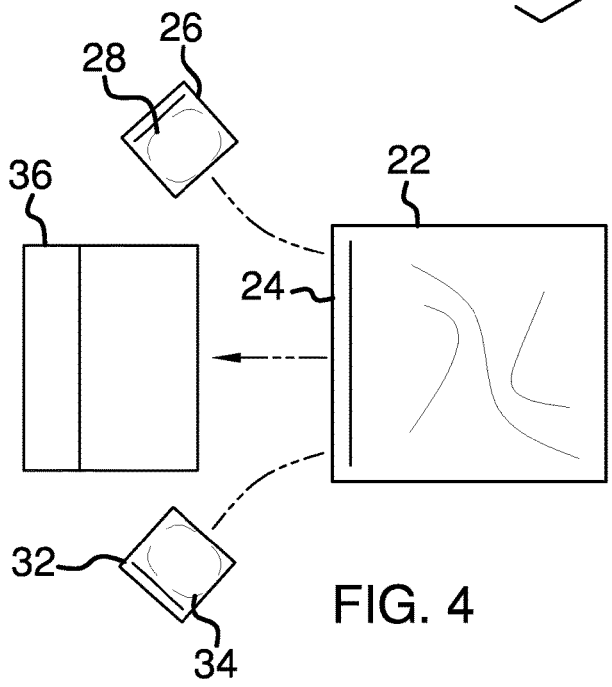

DIAPER CHANGING ASSEMBLY

BACKGROUND OF THE DISCLOSURE

Field of the Disclosure

The disclosure relates to diaper changing devices and more particularly pertains to a new diaper changing device for keeping diaper changing accessories with a diaper.

SUMMARY OF THE DISCLOSURE

An embodiment of the disclosure meets the needs presented above by generally comprising a bag removably coupled to a diaper. The bag is available when the diaper is changed. A first packet is positioned within the bag. The first packet contains a salve. The salve may be applied to a user when the diaper is changed. A second packet is positioned within the bag. The second packet contains a powder. The powder may be applied to the user when the diaper is changed. A plurality of wipes is positioned within the bag. The wipes may be used to clean the user when the diaper is changed.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 3 is a top perspective view of an embodiment of the disclosure.

FIG. 4 is a front view of an embodiment of the disclosure.

DESCRIPTION OF THE PREFERRED EMBODIMENT

Figure 1:
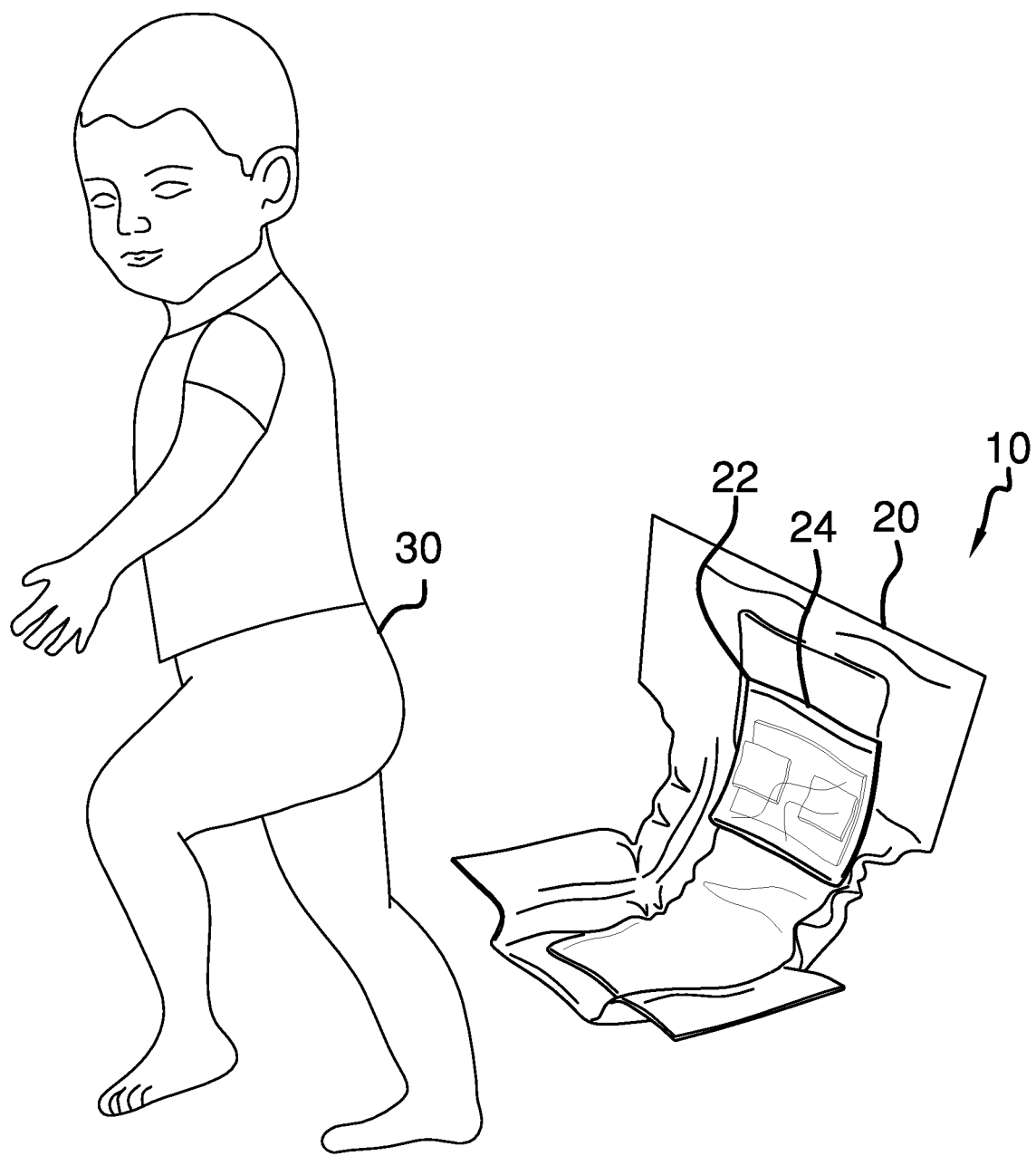
FIG. 1 is a perspective view of a diaper changing assembly according to an embodiment of the disclosure.
Figure 2:
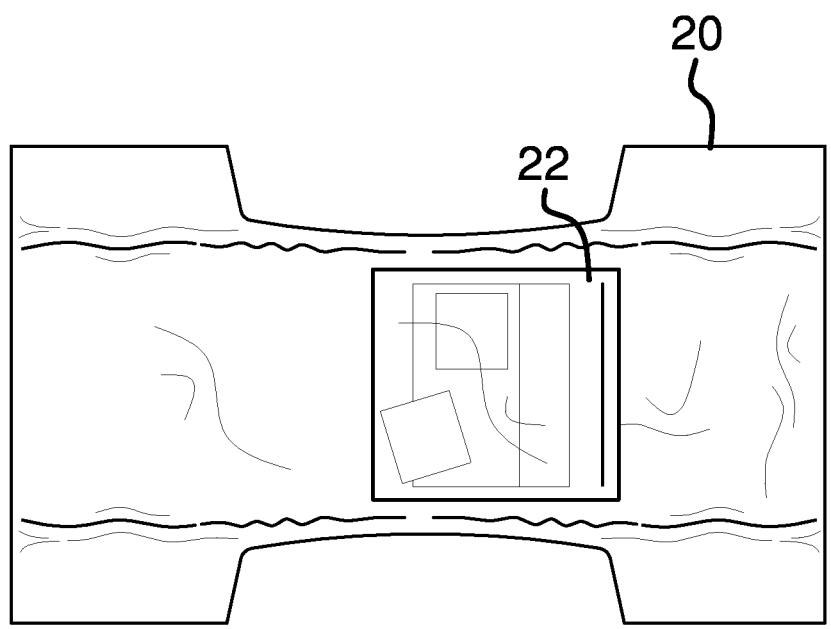
FIG. 2 is a top view of an embodiment of the disclosure.
Figure 5:
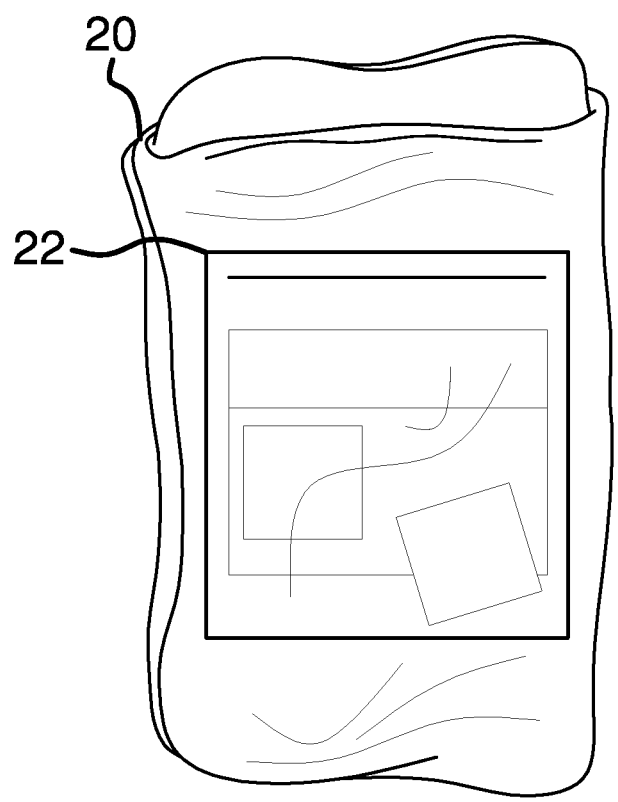
FIG. 5 is an in-use view of an embodiment of the disclosure.
Figure 6:
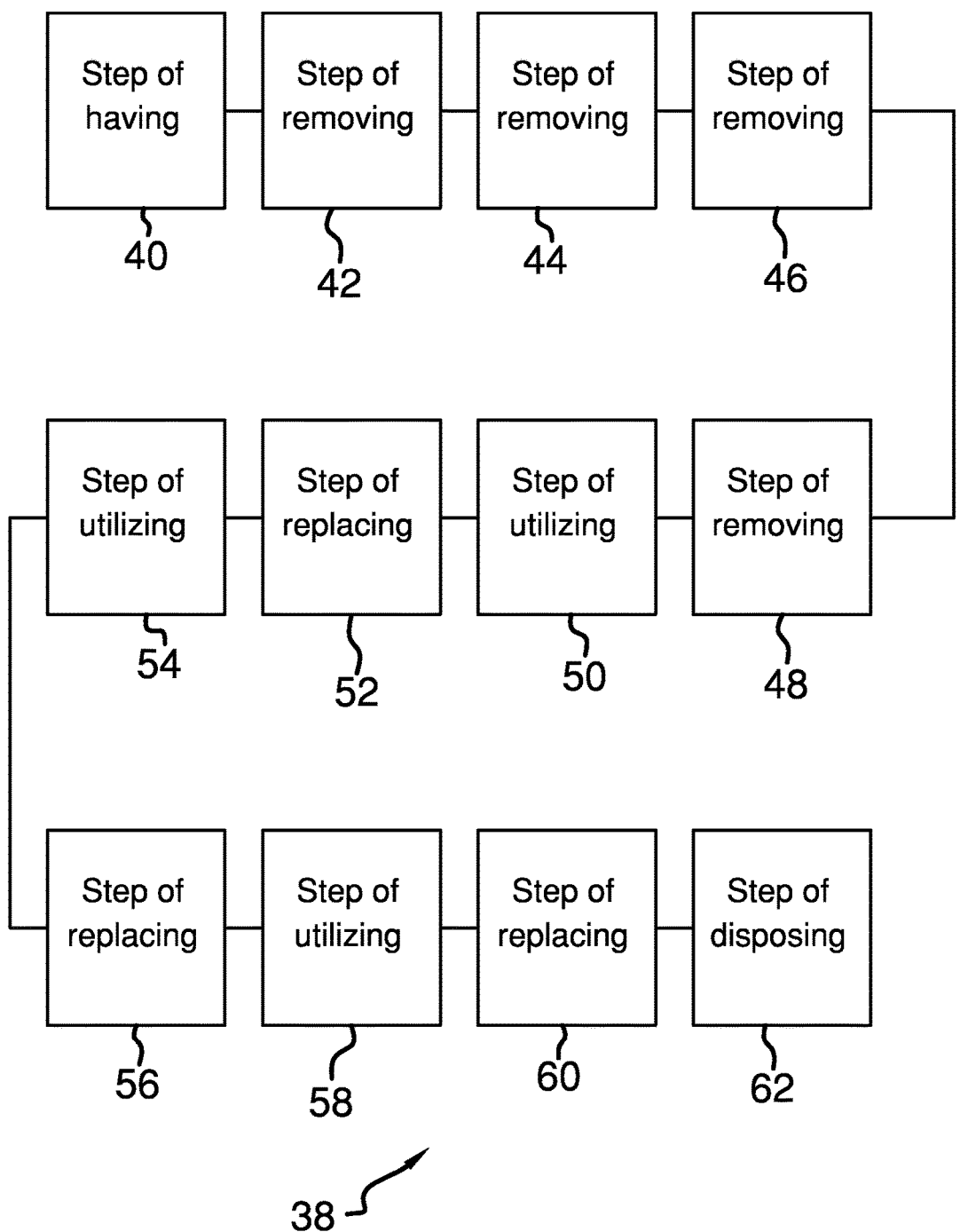
FIG. 6 is a schematic view of a method of utilizing an embodiment of the disclosure.

With reference now to the drawings, and in particular to FIGS. 1 through 6 thereof, a new diaper changing device embodying the principles and concepts of an embodiment of the disclosure and generally designated by the reference numeral 10 will be described.

As best illustrated in FIGS. 1 through 6, the diaper changing assembly 10 generally comprises a strip 12. The strip 12 has an adhesive 14 applied to each of a front side 16 and a back side 18 of the strip 12. The back side 18 of the strip 12 is removably adhered to a diaper 20. The diaper 20 may be a child's diaper of any conventional design.

A bag 22 is provided. A top 24 of the bag 22 is open. The bag 22 is removably adhered to the front side 16 of the strip 12. Additionally, the bag 22 is removably retained on the diaper 20. The bag 22 is available when the diaper 20 is put onto an infant 30.

A first packet 26 is positioned within the bag 22. The first packet 26 contains a salve 28. The first packet 26 is removable from the top 24 of the bag 22. Moreover, the salve 28 may be applied to a infant 30 when the diaper 20 is changed. The bag 22 may receive the first packet 26 after the salve 28 is utilized. The infant 30 may be a child.

A second packet 32 is positioned within the bag 22. The second packet 32 contains a powder 34. The second packet 32 is removable from the top 24 of the bag 22. Additionally, the powder 34 may be applied to the infant 30 when the diaper 20 is put on to the infant 30. The bag 22 may receive the second packet 32 after the powder 34 is utilized.

A plurality of wipes 36 is positioned within the bag 22. The wipes 36 are removable from the top 24 of the bag 22. Moreover, the wipes 36 may be used to clean the infant 30 when the diaper 20 is put onto the infant 30. The wipes 36 may be cleaning wipes of any conventional design.

The bag 22 may receive the wipes 36 after the wipes 36 are utilized. The bag 22 is removable from the diaper 20 when the diaper 20 is put onto the infant 30. Additionally, the bag 22 may be disposed of after the diaper 20 is applied to the infant 30.

In use, a method 38 of keeping diaper changing accessories with the diaper 20 includes a step 40 of having the strip 12 removably adhered to the diaper 20, the bag 22 removably adhered to the strip 12, the first packet 26 containing the salve 28 positioned within the bag 22, the second packet 32 containing the powder 34 positioned within the bag 22 and the plurality of wipes 36 positioned within the bag 22. The method 38 also includes a step 42 of removing the bag 22 and the strip 12 from the diaper 20. Additionally, the method 38 includes a step 44 of removing the first packet 26 from the bag 22. The method 38 includes a step 46 of removing the second packet 32 from the bag 22. Continuing, the method 38 includes a step 48 of removing the plurality of wipes 36 from the bag 22. The method 38 also includes a step 50 of utilizing the salve 28.

The method 38 includes a step 52 of replacing the first packet 26 within the bag 22. Moreover, the method 38 includes a step 54 of utilizing the powder 34. The method 38 additionally includes a step 56 of replacing the second packet 32 within the bag 22. Also, the method 38 includes a step 58 of utilizing the plurality of wipes 36. The method 38 includes a step 60 of replacing the plurality of wipes 36 within the bag 22. Finally, the method 38 includes a step 62 of disposing of the bag 22.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A diaper changing assembly comprising:
   a diaper;
   a strip having an adhesive applied to each of a front side and a back side of said strip, said back side of said strip being removably adhered to the diaper;
   a bag removably coupled to said diaper, said bag being removably adhered to said front side of said strip such that said bag is removably retained on the diaper;
   a first packet positioned within said bag, said first packet containing a salve configured to be applied to an infant when said diaper is put onto the infant;
   a second packet positioned within said bag, said second packet containing a powder configured to be applied to the infant when said diaper is put onto the infant;
   a plurality of wipes positioned within said bag, said wipes being configured to clean the infant when said diaper is put onto the infant.

2. The assembly according to claim 1, further comprising a top of said bag being open.

3. The assembly according to claim 2, further comprising said first packet being removable from said top of said bag, said bag being configured to receive said first packet after said salve is utilized.

4. The assembly according to claim 2, further comprising said second packet being removable from said top of said bag, said bag being configured to receive said second packet after said powder is utilized.

5. The assembly according to claim 2, further comprising said wipes being removable from said top of said bag, said bag being configured to receive said wipes after said wipes are utilized.

6. The assembly according to claim 1, further comprising said bag being removable from the diaper when the diaper is to be applied to the user such that said bag is configured to be disposed of after the diaper is applied to the user.

7. A diaper changing assembly comprising:
   a diaper;
   a strip having an adhesive applied to each of a front side and a back side of said strip, said back side of said strip being removably adhered to said diaper;
   a bag, a top of said bag being open, said bag being removably adhered to said front side of said strip such that said bag is removably retained on said diaper wherein said bag is configured to be available when said diaper is put onto an infant;
   a first packet positioned within said bag, said first packet containing a salve, said first packet being removable from said top of said bag, said salve being configured to be applied to the infant when said diaper is put onto the infant, said bag being configured to receive said first packet after said salve is utilized;
   a second packet positioned within said bag, said second packet containing a powder, said second packet being removable from said top of said bag, said powder being configured to be applied to the infant when the diaper is put onto the infant, said bag being configured to receive said second packet after said powder is utilized;
   a plurality of wipes positioned within said bag, said wipes being removable from said top of said bag, said wipes being configured to clean the infant when said diaper is put onto the infant, said bag being configured to receive said wipes after said wipes are utilized; and
   said bag being removable from said diaper when said diaper is to be applied to the infant such that said bag is configured to be disposed of after said diaper is put onto the infant.

8. A method of keeping diaper changing accessories with a diaper, the steps of the method comprising:
   having a strip removably adhered to a diaper, a bag removably adhered to said strip, a first packet containing a salve positioned within said bag, a second packet containing a powder positioned within said bag and a plurality of wipes positioned within said bag;
   removing said bag and said strip from the diaper;
   removing said first packet from said bag;
   removing said second packet from said bag;
   removing said plurality of wipes from said bag;
   utilizing said salve;
   replacing said first packet within said bag;
   utilizing said powder;
   replacing said second packet within said bag;
   utilizing said plurality of wipes;
   replacing said plurality of wipes within said bag; and
   disposing of said bag.

\* \* \* \* \*